United States Patent
Nakazato et al.

(10) Patent No.: US 6,479,674 B1
(45) Date of Patent: Nov. 12, 2002

(54) CARBOXYLIC ACID DERIVATIVES AND PROCESS FOR PRODUCING SAME

(75) Inventors: Atsuro Nakazato, Tokyo (JP); Toshihito Kumagai, Tokyo (JP); Kazunari Sakagami, Tokyo (JP); Kazuyuki Tomisawa, Tokyo (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/937,212

(22) PCT Filed: Feb. 21, 2000

(86) PCT No.: PCT/JP00/00969

§ 371 (c)(1), (2), (4) Date: Sep. 24, 2001

(87) PCT Pub. No.: WO00/58258

PCT Pub. Date: Oct. 5, 2000

(30) Foreign Application Priority Data

Mar. 25, 1999 (JP) .............................. 11-082608

(51) Int. Cl.[7] ...................... C07D 315/00; C07D 307/04
(52) U.S. Cl. ................... 549/426; 549/475; 556/437
(58) Field of Search ................... 556/437; 549/426, 549/475

(56) References Cited

U.S. PATENT DOCUMENTS

| | | | | |
|---|---|---|---|---|
| 5,912,248 | A | 6/1999 | Fernandez et al. | 514/256 |
| 5,958,960 | A | 9/1999 | Massey et al. | 514/393 |
| 6,160,009 | A | * 12/2000 | Massey et al. | 514/510 |
| 6,268,507 | B1 | * 7/2001 | Massey et al. | 548/301.4 |

FOREIGN PATENT DOCUMENTS

| | | | |
|---|---|---|---|
| EP | 0 774 454 A1 | 5/1997 | ......... C07C/229/50 |
| EP | 0 878 463 A1 | 11/1998 | ......... C07C/229/50 |
| JP | 2000-500754 | 1/2000 | ......... C07C/229/50 |
| JP | 2000-72731 | 3/2000 | ......... C07C/229/50 |
| WO | 97/17952 | 5/1997 | ......... A61K/31/195 |
| WO | 98/51655 | 11/1998 | ........... C07C/61/08 |

* cited by examiner

Primary Examiner—Joseph K. McKane
Assistant Examiner—Golam M. M. Shameem
(74) Attorney, Agent, or Firm—Sughrue Mion, PLLC

(57) ABSTRACT

The present invention relates to compounds which are useful for efficient synthesis of 2-amino-4-oxobicyclo[3.1.0] hexane-2,6-dicarboxylic acids.

The compounds according to the present invention comprise 2-oxobicyclo[3.1.0]hexane-6-carboxylic acid derivatives represented by the formula as follows:

$$R^2-Y^1 \diagdown\diagup CO_2R^1 \atop R^3-Y^2 \diagup \diagdown O \quad (1)$$

[wherein, $R^1$ represents a hydrogen atom, a $C_1$–$C_6$ alkyl group, a $C_3$–$C_6$ cycloalkyl group, a $C_3$–$C_6$ cycloalkyl $C_1$–$C_6$ alkyl group, an aryl group, an aryl $C_1$–$C_6$ alkyl group, a $C_1$–$C_6$ alkoxy $C_1$–$C_6$ alkyl group, a $C_1$–$C_6$ hydroxyalkyl group, a $C_1$–$C_6$ alkylthio $C_1$–$C_6$ alkyl group, a $C_1$–$C_6$ mercaptoalkyl group, a tetrahydrofuranyl group, or a tetrahydropyranyl group; $R^2$ and $R^3$ are identical or different, and each represents a $C_1$–$C_6$ alkyl group, a $C_3$–$C_6$ cycloalkyl group, a $C_3$–$C_6$ cycloalkyl $C_1$–$C_6$ alkyl group, an aryl group, or an aryl $C_1$–$C_6$ alkyl group, or alternatively, $R^2$ and $R^3$ together represent —$(CH_2)_n$— (wherein n represents 2 or 3); and $Y^1$ and $Y^2$ are identical or different, and each represents a sulfur atom, an oxygen atom, or a nitrogen atom].

2 Claims, No Drawings

CARBOXYLIC ACID DERIVATIVES AND PROCESS FOR PRODUCING SAME

This application is a 371 of PCT/00/00969 Feb. 21, 2000.

FIELD OF TECHNOLOGY

The present invention relates to 2-oxobicyclo[3.1.0]hexane-6-carboxylic acid derivatives and to a process for producing the same.

BACKGROUND ART

The metabotropic glutamate receptors, which correspond to one type of glutamate receptors, are classified pharmacologically into three groups. Of these, those in group 2 (mGluR2/mGluR3) bind with adenylcyclase and inhibit the accumulation of the Forskolin stimulation of cyclic adenosine monophosphate (cAMP) (Trends Pharmacol. Sci., 14, 13 (1993)), and for this reason, it is suggested that the compounds acting on group 2 metabotropic glutamate receptors have treatment effects and prevention effects on psychiatric disorders such as, for example, schizophrenia, anxiety and its associated diseases, depression, bipolar disorder, and epilepsy; and on neurological diseases such as drug dependence, cognitive disorders, Alzheimer's disease, Huntington's chorea, Parkinson's disease, dyskinesia associated with muscular rigidity, cerebral ischemia, cerebral failure, myelopathy, and head trauma.

The present inventors discovered 2-amino-4-oxobicyclo[3.1.0]hexane-2,6-dicarboxylic acid (7) as one of the useful compounds acting on group 2 metabotropic glutamate receptors (Japanese Patent Application No. Hei 10-246344). In the specification of Japanese Patent Application No. Hei 10-246344, as apreparation method thereof, a synthesis method as described below is proposed. The synthesis method comprises the steps of adding benzyl alcohol to an enone derivative (8) to yield a benzyloxy compound (9), subsequently subjecting the compound (9) to hydantoination to yield a hydantoin derivative (10), subsequently subjecting the derivative (10) to debenzylation, oxidation, and thioketalation to yield a thioketal-hydantoin derivative (11), followed by hydrolysis (in the reaction schemes described below, $R^2$, $R^3$, and $R^5$ are identical or different, each represents a lower alkyl group having 1 to 10 carbon atoms, with the proviso that $R^2$ and $R^3$ together may represent —$(CH_2)_n$— (wherein n represents 2 or 3)).

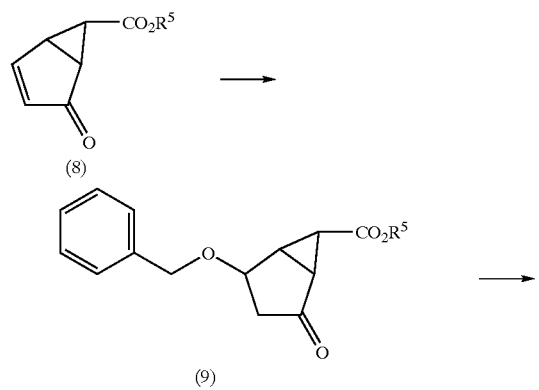

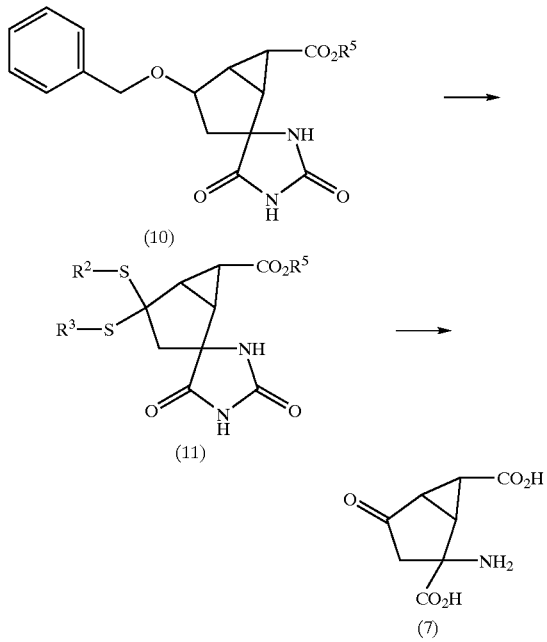

DISCLOSURE OF THE INVENTION

An objective of the present invention is to provide novel intermediates which are useful for efficient synthesis of 2-amino-4-oxobicyclo[3.1.0]hexane-2,6-dicarboxylic acid acting on group 2 metabotropic glutamate receptors, which has treatment effects and prevention effects on psychiatric disorders such as schizophrenia, anxiety and its associated diseases, depression, bipolar disorder, and epilepsy, and neurological disorders such as drug dependence, cognitive disorders, Alzheimer's disease, Huntington's chorea, Parkinson's disease, dyskinesia associated with muscular rigidity, cerebral ischemia, cerebral failure, myelopathy, and head trauma, and a process for producing the same.

As a result of diligent research, the present inventors discovered that a 2-oxobicyclo [3.1.0]hexane-6-carboxylic acid derivative (1), which may be synthesized using, as a starting material, 4-hydroxy-2-cyclopentenone, or the hydroxy-group-protected compound thereof, which is easily derived from furfuryl alcohol, is useful for an efficient synthesis of 2-amino-4-oxobicyclo[3.1.0]hexane-2,6-dicarboxylic acid (7), and completed the present invention.

That is, one mode of the present invention corresponds to a 2-oxobicyclo[3.1.0]hexane-6-carboxylic acid derivative represented by formula (1)

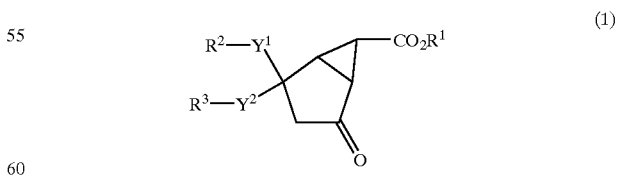

[wherein, $R^1$ represents a hydrogen atom, a $C_1$–$C_6$ alkyl group, a $C_3$–$C_6$ cycloalkyl group, a $C_3$–$C_6$ cycloalkyl $C_1$–$C_6$ alkyl group, an aryl group, an aryl $C_1$–$C_6$ alkyl group, a $C_1$–$C_6$ alkoxy $C_1$–$C_6$ alkyl group, a $C_1$–$C_6$ hydroxyalkyl group, a $C_1$–$C_6$ alkylthio $C_1$–$C_6$ alkyl group, a $C_1$–$C_6$ mercaptoalkyl group, a tetrahydrofuranyl group, or a tetrahydropyranyl group; $R^2$ and $R^3$ are identical or different, and each represents a $C_1$–$C_6$ alkyl group, a $C_3$–$C_6$ cycloalkyl group, a $C_3$–$C_6$ cycloalkyl $C_1$–$C_6$ alkyl group, an aryl group, or an aryl $C_1$–$C_6$ alkyl group, or alternatively, $R^2$ and $R^3$ together represent —$(CH_2)_n$— (wherein n represents 2 or 3); and $Y^1$ and $Y^2$ are identical or different, and each represents a sulfur atom, an oxygen atom, or a nitrogen atom].

In addition, another mode of the present invention corresponds to a process for producing a 2-oxobicyclo[3.1.0]hexane-6-carboxylic acid derivative (1), comprising the steps of:

reacting a cyclopentenone derivative represented by formula (2)

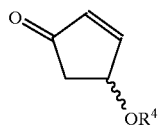

(2)

[wherein, $R^4$ represents a hydrogen atom or a protecting group of the hydroxyl group]
with a sulfonium ylide represented by $Me_2S=CHCO_2R^5$ [wherein, $R^5$ represents a $C_1$–$C_6$ alkyl group, a $C_3$–$C_6$ cycloalkyl group, a $C_3$–$C_6$ cycloalkyl $C_1$–$C_6$ alkyl group, an aryl group, an aryl $C_1$–$C_6$ alkyl group, a $C_1$–$C_6$ alkoxy $C_1$–$C_6$ alkyl group, a $C_1$–$C_6$ hydroxyalkyl group, a $C_1$–$C_6$ alkylthio $C_1$–$C_6$ alkyl group, a $C_1$–$C_6$ mercaptoalkyl group, a tetrahydrofuranyl group, or a tetrahydropyranyl group] or alternatively, with a sulfonium salt represented by $Me_2S^+CH_2CO_2R^5 \cdot X^-$ [wherein, $R^5$ is the same as described above; and X represents a chlorine atom, a bromine atom, or an iodine atom]
to yield a bicyclo compound represented by formula (3)

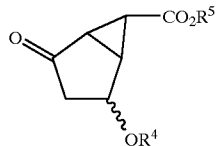

(3)

[wherein, $R^4$ and $R^5$ are the same as described above]; protecting the carbonyl group of said bicyclo compound to yield a derivative represented by formula (4)

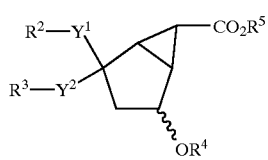

(4)

[wherein, $R^2$ and $R^3$ are identical or different, and each represents a $C_1$–$C_6$ alkyl group, a $C_3$–$C_6$ cycloalkyl group, a $C_3$–$C_6$ cycloalkyl $C_1$–$C_6$ alkyl group, an aryl group, or an aryl $C_1$–$C_6$ malkyl group, or alternatively, $R^2$ and $R^3$ together represent —$(CH_2)_n$— (wherein n represents 2 or 3); $Y^1$ and $Y^2$ are identical or different, and each represents a sulfur atom, an oxygen atom, or a nitrogen atom; and $R^4$ and $R^5$ are the same as described above]; and oxidizing said derivative wherein $R^4$ represents a hydrogen atom, with the proviso that in the case of $R^4$ of said derivative representing a group other than a hydrogen atom, the $R^4$ is converted into a hydrogen atom beforehand.

Furthermore, another mode of the present invention corresponds to a bicyclo[3.1.0]hexane-6-carboxylic acid derivative, which may be derived from the carboxylic acid derivative (1), represented by formula (5)

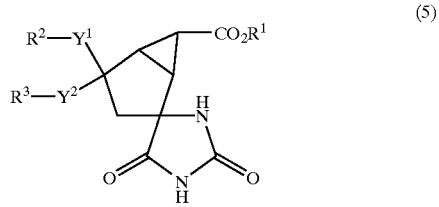

(5)

[wherein, $R^1$ represents a hydrogen atom, a $C_1$–$C_6$ alkyl group, a $C_3$–$C_6$ cycloalkyl group, a $C_3$–$C_6$ cycloalkyl $C_1$–$C_6$ alkyl group, an aryl group, an aryl $C_1$–$C_6$ alkyl group, a $C_1$–$C_6$ alkoxy $C_1$–$C_6$ alkyl group, a $C_1$–$C_6$ hydroxyalkyl group, a $C_1$–$C_6$ alkylthio $C_1$–$C_6$ alkyl group, a $C_1$–$C_6$ mercaptoalkyl group, a tetrahydrofuranyl group, or a tetrahydropyranyl group; $R^2$ and $R^3$ are identical or different, and each represents a $C_1$–$C_6$ alkyl group, a $C_3$–$C_6$ cycloalkyl group, a $C_3$–$C_6$ cycloalkyl $C_1$–$C_6$ alkyl group, an aryl group, or an aryl $C_1$–$C_6$ alkyl group, or alternatively, $R^2$ and $R^3$ together represent —$(CH_2)_n$— (wherein n represents 2 or 3); and $Y^1$ and $Y^2$ are identical or different, and each represents. a sulfur atom, an oxygen atom, or a nitrogen atom].

The terms used in the present invention are defined in the following. In the present invention, "$C_n$–$C_m$" means that the group following the "$C_n$–$C_m$" has from n to m carbon atoms.

The $C_1$–$C_6$ alkyl group means a straight-chain or branched-chain alkyl group having 1 to 6 carbon atoms, examples of which include, for example, a methyl group, an. ethyl group, a propyl group, an isopropyl group, a butyl group, an isobutyl group, a t-butyl group, a pentyl group, an isopentyl group, a hexyl group, an isohexyl group, and the like.

The $C_3$–$C_6$ cycloalkyl group means a cyclic alkyl group having 3 to 6 carbon atoms, examples of which include, for example, a cyclopropyl group, a cyclopentyl group, a cyclohexyl group, or the like.

The $C_3$–$C_6$ cycloalkyl $C_1$–$C_6$ alkyl group means a group having a combined structure of a $C_3$–$C_6$ cycloalkyl group and a $C_1$–$C_6$ alkyl group, examples of which include, for example, a cyclopropylmethyl group, a cyclobutylmethyl group, a cyclopentylmethyl group, a cyclohexylmethyl group, and the like.

The aryl group means a phenyl group, a naphthyl group, or the like, and is preferably a phenyl group. The aryl $C_1$–$C_6$ alkyl means a straight-chain or branched-chain alkyl group having 1 to 6 carbon atoms, substituted with at least one aryl group, and preferably a phenyl group. Examples thereof include, for example, a benzyl group, a diphenylmethyl group, a 1-phenylethyl group, a 2-phenylethyl group, and the like.

The $C_1$–$C_6$ alkoxy $C_1$–$C_6$ alkyl group means a group having a combined structure of a $C_{1-6}$ alkoxy group and a $C_{1-6}$ alkyl group. The $C_1$–$C_6$ alkoxy group means a straight-chain or branched-chain alkoxy group having 1 to 6 carbon atoms, examples of which include, for example, a methoxy group, an ethoxy group, a propoxy group, an isopropoxy group, a butoxy group, an isobutoxy group, a t-butoxy group, a pentyloxy group, an isopentyloxy group, or the like. Therefore, examples of the $C_1$–$C_6$ alkoxy $C_1$–$C_6$ alkyl groups include a methoxymethyl group, an ethoxymethyl group, a methoxyethyl group, an ethoxyethyl group, a propoxyethyl group, an isopropoxyethyl group, a butoxyethyl group, an isobutoxyethyl group, a pentyloxyethyl group, an isopentyloxyethyl group, and the like.

The $C_1$–$C_6$ hydroxyalkyl group means a $C_{1-6}$ alkyl group substituted with at least one hydroxyl group. Therefore, examples of the $C_1$–$C_6$ hydroxyalkyl group include, for example, a 2-hydroxyethyl group, a 3-hydroxypropyl group, a 2,3-dihydroxypropyl group, and the like.

The $C_1$–$C_6$ alkylthio $C_1$–$C_6$ alkyl group means a group having a combined structure of a $C_1$–$C_6$ alkylthio group and a $C_1$–$C_6$ alkyl group. The $C_1$–$C_6$ alkylthio group means a straight-chain or branched-chain alkylthio group having 1 to 6 carbon atoms, examples of which include, for example, a methylthio group, an ethylthio group, a propylthio group, an isopropylthio group, a butylthio group, an isobutylthio group, a t-butylthio group, a pentylthio group, an isopentylthio group, and the like. Therefore, examples of the $C_1$–$C_6$ alkylthio $C_1$–$C_6$ alkyl group include a methylthiomethyl group, a 2-methylthioethyl group, and the like.

The $C_1$–$C_6$ mercaptoalkyl group means a $C_1$–$C_6$ alkyl group substituted with at least one mercapto group. Therefore, examples of the $C_1$–$C_6$ mercaptoalkyl group include a 2-mercaptoethyl group, a 3-mercaptopropyl group, a 2,3-dimercaptopropyl group, and the like.

In each group described above, at least one hydrogen atom on the group may be substituted with an atom or with another group, which is not a hydrogen atom, for example, a halogen atom such as a fluorine atom, a chlorine atom, a bromine atom, or an iodine atom; a nitro group; an amino group; a hydroxyl group; a thiol group; a formyl group; a carboxyl group; a cyano group; a carbamoyl group; an alkyl group such as a methyl group, an ethyl group, a propyl group, an isopropyl group, a butyl group, an isobutyl group, a sec-butyl group, a tert-butyl group, a pentyl group, an isopentyl group, a neopentyl group, or a tert-pentyl group; an aryl group and a heterocyclic group such as a phenyl group, a naphthyl group, a biphenyl group, an anthranyl group, a pyrrolyl group, a pyridyl group, or a thienyl group; an alkoxycarbonyl group such as a methoxycarbonyl group, or an ethoxycarbonyl group; an acyl group such as an acetyl group, or a benzoyl group; an alkoxy group such as a methoxy group, an ethoxy group, or a propoxy group; or an alkylthio group such as a methylthio group, an ethylthio group, or a propylthio group. Therefore, for example, a 2,2,2-trichloroethyl group, a phenacyl group, a 2,6-dimethylcyclohexyl group, and a 4-methoxybenzyl group, and the like are also included in the scope of $R^1$ and $R^2$. The number of the carbon atoms in these substituents is not included in the numbers n or m described above.

In the present invention, the protecting group of a shydroxyl group includes protecting groups which are commonly used, such as an acyl group or a trisubstituted silyl group, in addition to the $C_1$–$C_6$ alkyl group, the $C_3$–$C_6$ cycloalkyl group, the $C_3$–$C_6$ cycloalkyl $C_1$–$C_6$ alkyl group, the aryl group, the aryl $C_1$–$C_6$ alkyl group, the $C_1$–$C_6$ alkoxy $C_1$–$C_6$ alkyl group, the $C_1$–$C_6$ hydroxyalkyl group, the $C_1$–$C_6$ alkylthio $C_1$–$C_6$ alkyl group, the $C_1$–$C_6$ mercaptoalkyl group, the tetrahydrofuranyl group, and the tetrahydropyranyl group, as described above. Here, the acyl group refers to a straight-chain or branched-chain $C_1$–$C_6$ aliphatic or aromatic acyl group. Examples thereof include, for example, an acetyl group, a pivaloyl group, benzoyl group, and the like. In addition, the trisubstituted silyl group refers to a silyl group having three arbitrary substituents selected from an alkyl group having 1 to 6 carbon atoms and a phenyl group. Examples thereof include, for example, a trimethylsilyl group, a triethylsilyl group, a tert-butyldimethylsilyl group, a tert-butyldiphenylsilyl group, and the like.

In the compounds represented by formula (1), in the case where $R^2$—$Y^1$— and $R^3$—$Y^2$— represent the identical group, or in the case where $Y^1$ and $Y^2$ are identical and $R^2$ and $R^3$ together represent —$(CH_2)_n$— (wherein n represents 2 or 3), three asymmetric carbon atoms are present at the 1-position, 5-position, and 6-position. In addition, in the case where $Y^1$ or $Y^2$, or alternatively, $R^2$ or $R^3$ is different, four asymmetric carbon atoms are present at the 1-position, 4-position, 5-position, and 6-position. Therefore, the compounds of the present invention may be present as optically active substances, enantiomer mixtures such as racemic bodies, or diastereomer mixtures. That is, the compounds of the present invention include all of the optically active substances, the enantiomer mixtures such as racemic bodies, and the diastereomer mixtures, of the compounds represented by formula (1).

DETAILED DESCRIPTION OF THE INVENTION

The compounds of formula (1) according to the present invention may be produced according to the reactions described below (in the following reaction schemes, $R^1$, $R^2$, $R^3$, $R^4$, $R^5$ $Y^1$, and $Y^2$ are the same as described above).

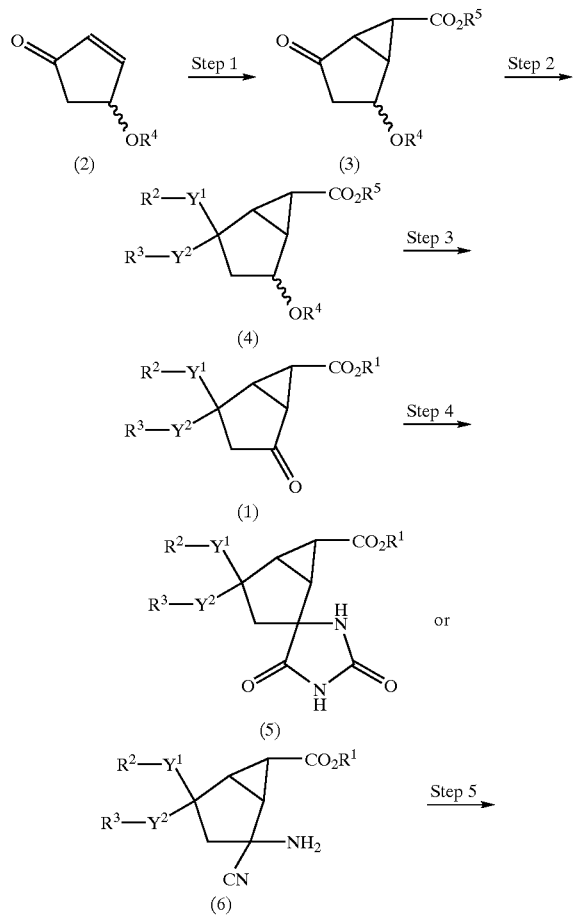

-continued

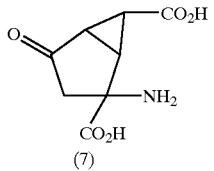

(7)

Step 1: By reacting an enone derivative (2) (see Japanese Unexamined Patent Application, First Publication No. Sho 57-62236) produced by one step (in the case where $R^4$ represents a hydrogen atom) or two steps (in the case where $R^4$ represents a group other than a hydrogen atom) from furfuryl alcohol, with a sulfonium ylide represented by $Me_2S=CHCO_2R^5$ [wherein, $R^5$ is the same as described above] which is previously prepared, in an inert solvent, or alternatively, with a sulfonium salt represented by $Me_2S^+CH_2CO_2R^5 \cdot X^-$ [wherein, $R^5$ is the same as described above; and X represents a chlorine atom, a bromine atom, or an iodine atom] in the presence of a base in an inert solvent to yield a bicyclo compound (3).

As the inert solvent, for example, hydrocarbon type solvents such as benzene, toluene, and hexane; halogen type solvents such as dichloromethane and chloroform; ether type solvents such as tetrahydrofuran and diethyl ether; acetonitrile; a mixture of these solvents; and the like may be employed. In addition, as the base, for example, organic bases such as triethylamine, diisopropylethylamine, pyridine, and 1,8-diazabicyclo[5.4.0]-7-undecene; or inorganic bases such as potassium carbonate or sodium hydroxide may be employed. It is preferable that the present reaction be carried out at a temperature of 0 to 30° C. In addition, it is preferable that the reaction be continued for 12 hours to 3 days, in the case where the sulfonium ylide represented by $Me_2S=CHCO_2R^5$ is employed.

Step 2: The carbonyl group moiety of the bicyclo compound (3) is protected according to a common method as described in Protecting Groups in Organic Synthesis (written by Theodora W. Greene, John Wilely & Sons Inc.) to yield a derivative (4). As the protecting form for a carbonyl group, a common cyclic or acyclic protecting form such as, for example, dimethyl ketal, diethyl ketal, 1,3-dioxane, 1,3-dioxoran, S,S'-dimethyl ketal, 1,3-dithiane, 1,3-dithioran, 1,3-oxathioran, oxazolidine, N-methyloxazolidine, or the like may be employed.

In the case where $R^4$ is a protecting group, such as a silyl type protecting group, which can be easily substituted with a hydrogen atom in the presence of a Lewis acid, at the same time as carrying out the protection for the carbonyl group moiety in the presence of a Lewis acid such as boron trifluoride diethyl ether complex, the protecting group of the hydroxyl group is deprotected to yield $R^4$=H.

Step 3: In the case where $R^4$ is other than a hydrogen atom in the derivative (4), the protecting group $R^4$ of the hydroxyl group is deprotected to yield $R^4$=H, followed by oxidation to derive a (±)-2-oxobicyclo[3.1.0]hexane-6-carboxylic acid derivative (1) which is the compound of the present invention. Here, the deprotection of the protecting group $R^4$ of the hydroxyl group, for example in the case where $R^4$ is an acyl type protecting group, can be carried out in the presence of an inorganic base such as potassium carbonate or sodium hydroxide in alcohol type solvents such as methanol or ethanol, ketones such as acetone or methyl ethyl ketone, ether type solvents such as tetrahydrofuran, water, or a mixture of these organic solvents and water. In addition, for example, in the case where $R^4$ is a benzyl group, the deprotection thereof can be carried out by, for example, hydrogenation using palladium as a catalyst, Birch reduction, or the like. Furthermore, for example, in the case where $R^4$ is a silyl type protecting group, the deprotection thereof can be carried out using a desilylation agent such as tetra-n-butylammonium fluoride (see Protecting Groups in Organic Synthesis (written by Theodora W. Greene, John Wilely & Sons Inc.)).

Here, the oxidation refers to reacting oxidants such as chromium type oxidants represented by a Jones oxidation reagent, Collins oxidation reagent, pyridinium chlorochromate (PCC), pyridinium dichromate (PDC), or the like; manganese type oxidants such as potassium permanganate or manganese dioxide; dimethylsulfoxide type oxidants employing, for example, oxalylchloride, acetic anhydride, diphosphorus pentaoxide, sulfur trioxide—pyridine, or the like, as activating agents; oxygen oxidation employing, for example, palladium, platinum, or the like as a catalyst; cerium type oxidants such as cerium diammonium nitrate or cerium sulfate; ruthenium type oxidants such as tetrapropylammonium perruthenate or ruthenium oxide; oxidants such as a Dess-Martin reagent (see Oxidations in Organic Chemistry, American Chemical Society, Washington, D.C., 1990, written by Milos Hudlicky); and the like, in an inert solvent such as ethers such as tetrahydrofuran or diethyl ether; hydrocarbons such as toluene or benzene; halogen type solvents such as dichloromethane or chloroform; ketones such as acetone or ethyl methyl ketone; acetonitrile; N,N-dimethylformamide; acetic acid; pyridine; water; or mixed solvents thereof.

Here, in the case where $R^1$ is a lower alkyl group or a benzyl group, the $R^1$ can be converted to a hydrogen atom by hydrolysis of an ester under acidic or basic conditions. In addition, in the case where $R^1$ is a benzyl group, the $R^1$ can be converted to a hydrogen atom by hydrogenation.

The carboxylic acid derivatives (1) of (±) configurations can be optically resolved into (+) and (−) configurations by the HPLC method employing chiral carriers such as cellulose carbamate derivatives or amylose carbamate derivatives. In addition, in the case where $R^1$ is a hydrogen atom, the carboxylic acid derivatives (1) of (±) configurations can be optically resolved into (+) and (−) configurations by using optically active amines such as (+)- or (−)-1-phenylethylamine, (+)- or (−)-phenylglycinol, (+)- or (−)-2-amino-1-butanol, (+)- or (−)-alaninol, brucine, cinchonidine, cinchonine, quinine, quinidine, or dehydroabiethylamine, or alternatively, by deriving the amide derivatives with optically active primary or secondary amines.

In the 2-oxobicyclo[3.1.0]hexane-6-carboxylic acid derivatives (1), by converting the carbonyl group moiety protected by the couple of $R^2-Y^1$ and $R^3-Y^2$ and the non-protected carbonyl group moiety mutually, as shown in the scheme described below, the carboxylic acid derivatives (1) of (−) configuration may be converted into the compounds (12) equivalent to the derivatives (1) of (+) configuration, and the carboxylic acid derivatives (1) of (+) configuration may be converted into the compounds (12) equivalent to the derivatives (1) of (−) configuration. (In the following formulae, $R^1$, $R^2$, $R^3$, $Y^1$, and $Y^2$ are the same as described above; $R^6$ and $R^7$ are the same groups as defined in $R^2$ and $R^3$; and $Y^3$ and $Y^4$ are the same groups as defined in $Y^1$ and $Y^2$.)

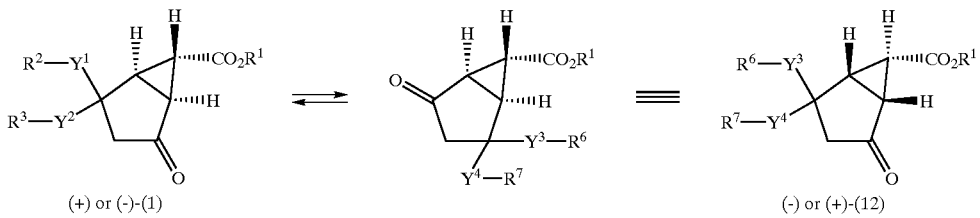

(+) or (-)-(1)            (-) or (+)-(12)

Therefore, each of (+) and (−) optically active substances resolved from the (±) configurations can be effectively utilized for synthesis of optically active substances of 2-amino-4-oxobicyclo[3.1.0]hexane-2,6-dicarboxylic acids (7). As described above, the carboxylic acid derivatives (1) of the present invention are extremely useful for synthesis of the optically active 2-amino-4-oxobicyclo[3.1.0]hexane-2, 6-dicarboxylic acids (7).

Such conversions may be carried out in the following manner. That is, for example, in the case where $R^2-Y^1-$ and $R^3-Y^2-$, which protect one carbonyl group, together represent a $-SCH_2CH_2S-$ group, while another carbonyl group which is present in a non-protected state is protected by a $-OCH_2CH_2O-$ group, the only $-SCH_2CH_2S-$ group is selectively deprotected (see Protecting Groups in organic Synthesis (written by Theodora W. Greene, John wilely & Sons Inc.)). As a result, the carbonyl group which is first protected by a $-SCH_2CH_2S-$ group enters a non-protected state, and on the other hand, the carbonyl group which is first in a non-protected state is protected by a $-OCH_2CH_2O-$ group. By changing the protecting position of the carbonyl groups of the optically active carboxylic acid derivatives (1), as described above, the carboxylic acid derivatives (1) can be effectively utilized.

The carboxylic acid derivatives (1) of the present invention may be converted into the 2-amino-4-oxobicyclo[3.1.0] hexane-2,6-dicarboxylic acids (7), for example, via the following steps.

Step 4: (±)-, (+)-, or (−)-carboxylic acid derivatives (1) yield hydantoin derivatives (5) or aminocyanide derivatives (6) by Strecker Amino Acid Synthesis (Ann., 75, 27 (1850); and Ann., 91, 349 (1850)), Bucherer-Bergs Reaction (J. Prakt. Chem., 140, 69 (1934)), or the modified methods thereof.

Step 5: The hydantoin derivatives (5) or aminocyanide derivatives (6) yield (±)-, (+)-, or (−)-2-amino-4-oxobicyclo [3.1.0]hexane-2,6-dicarboxylic acids (7) by deprotection of the carbonyl group moiety protected by the couple of $R^2-Y^1-$ and $R^3-Y^2-$, and hydrolysis.

Here, said hydrolysis may be carried out under acidic conditions employing acids such as hydrochloric acid, hydrobromic acid, or sulfuric acid, or under basic conditions employing bases such as sodium hydroxide, potassium hydroxide, or barium hydroxide. In addition, with regard to the deprotection of the protecting group of the carbonyl group moiety, common deprotecting conditions may be appropriately employed (see Protecting Groups in Organic Synthesis (written by Theodora W. Greene, John Wilely & Sons Inc.)). Furthermore, for example, in the case where $R^2-Y^1-$ and $R^3-Y^2-$ together represent a $-SCH_2CH_2S-$ group, the $-SCH_2CH_2S-$ group may be removed at the same time as hydrolysis of the hydantoin or aminocyanide moiety, for example, by employing acid hydrolysis conditions with sulfuric acid.

Since the 2-amino-4-oxobicyclo[3.1.0]hexane-2,6-dicarboxylic acids (7) have four asymmetric carbon atoms at the 1-position, 2-position, 5-position, and 6-position, they may exist as optically active substances, two kinds of enantiomer mixtures of racemic bodies, and diastereomer mixtures. Here, said diastereomers may be resolved by a common means such as column chromatography using silica gel, recrystallization, or the like. Each resolved diastereomer may be resolved into the corresponding enantiomers by common resolving methods such as a resolving method using a basic chiral resolving agent. Here, the basic chiral resolving agent refers to optically active amines such as (+)- or (−)-1-phenylethylamine, (+)- or (−)-2-amino-1-butanol, (+)- or (−)-alaninol, brucine, cinchonidine, cinchonine, quinine, quinidine, or dehydroabiethylamine.

The 2-amino-4-oxobicyclo[3.1.0]hexane-2,6-dicarboxylic acids (7) obtained as described above may be employed as pharmaceutical compositions by combining with, for example, carriers, diluents, excipients, or the like, in the form of pharmaceutically acceptable salts or hydrates. Here, as an example of the pharmaceutically acceptable salts, mention may be made of salts with inorganic acids such as sulfuric acid, hydrochloric acid, or phosphoric acid; salts with organic acids such as acetic acid, oxalic acid, lactic acid, tartaric acid, fumaric acid, maleic acid, methanesulfonic acid, or benzenesulfonic acid; salts with amines such as trimethylamine or methylamine; salts with metal ions such as sodium ion, potassium ion, or calcium ion; or the like.

EXAMPLES

In the following, representative examples of the present invention are described. However, it should be understood that the present invention is not limited to these examples.

Example 1

Syntheses of Ethyl (1SR,4RS,5RS,6SR)-4-tert-Butyldimethylsilyloxy-2-oxobicyclo[3.1.0]hexane-6-carboxylate and Ethyl (1SR,4SR,5RS,6SR)-4-tert-Butyldimethylsilyloxy-2-oxobicyclo[3.1.0]hexane-6-carboxylate A toluene (60 mL) solution of 18 g of 4-tert-butyldimethylsilyloxy-2-cyclopentenone was added to a toluene (120 mL) solution of 13.6 g of ethyl (dimethylsulfanilidene-)acetate with ice-cooling. The reaction mixture was stirred for 6 hours at room temperature. In addition, a toluene (120 mL) solution of 24.0 g of ethyl (dimethylsulfanilidene)acetate was added to the reaction mixture at 0° C. The reaction mixture was stirred for one day at room temperature, and subsequently was poured into 1N hydrochloric acid to separate it into two layers. The organic layer was dried over anhydrous sodium sulfate. After the desiccant was filtered off, the filtrate was concentrated under reduced pressure. There side was purified by silica gel column chromatography (Wako gel C200 (produced by Wako Pure Chemical Industries Ltd.), eluent: hexane-ethyl acetate=15:1) to yield 19.0 g of a mixture of ethyl (1SR, 4RS,5RS,6SR)-4-tert-butyldimethylsilyloxy-2-oxobicyclo[3.1.0]hexane-6-carboxylate and ethyl (1SR,4SR,5RS,6SR)-4-tert-butyldimethylsilyloxy-2-oxobicyclo[3.1.0]hexane-6-carboxylate.

The $^1$H-NMR spectral data of the obtained compounds are shown below.

$^1$H-NMR (CDCl$_3$) δ (ppm); 0.08 (3H×5/8, s), 0.11 (3H×3/8, s), 0.90 (9H×5/8, s), 0.92 (9H×3/8, s), 1.27 (3H, t, J=7.3 Hz), 1.85 (1H×5/8, dd, J=3.5, 2.6 Hz), 1.92–2.70 (4H+1H×3/8, m), 4.17 (2H×5/8, q, J=7.3 Hz), 4.20 (2H×3/8, q, J=7.3 Hz), 4.52 (1H×5/8, d, J=4.8 Hz), 4.73 (1H×3/8, m).

Example 2

Syntheses of Ethyl (1RS,4RS,5RS,6RS)-2,2-Ethylenedithio-4-hydroxybicyclo[3.1.0]hexane-6-carboxylate and Ethyl (1RS,4SR,5RS,6RS)-2,2-Ethylenedithio-4-hydroxybicyclo[3.1.0]hexane-6-carboxylate The following reaction was carried out under a nitrogen atmosphere. Boron trifluoride diethyl ether complex in an amount of 2.1 mL was added to a methylene chloride (168 mL) solution of 16.8 g of a mixture of ethyl (1SR,4RS,5RS,6SR)-4-tert-butyldimethylsilyloxy-2-oxobicyclo[3.1.0]hexane-6-carboxylate and ethyl (1SR,4SR,5RS,6SR)-4-tert-butyldimethylsilyloxy-2-oxobicyclo[3.1.0]hexane-6-carboxylate and 5.7 mL of ethanedithiol at room temperature. The reaction mixture was stirred for 2 days and was subsequently concentrated under reduced pressure. The residue was separated into two layers using a saturated aqueous solution of sodium hydrogencarbonate and chloroform. The organic layer was dried over anhydrous sodium sulfate. After the desiccant was filtered off, the filtrate was concentrated under reduced pressure. The residue was purified by silica gel column chromatography (Wako gel C200 (produced by Wako Pure Chemical Industries Ltd.), eluent: hexane-ethyl acetate=4:1 to 2:1) to yield 13.7 g of a mixture of ethyl (1RS,4RS,5RS,6RS)-2,2-ethylenedithio-4-hydroxybicyclo[3.1.0]hexane-6-carboxylate and ethyl (1RS,4SR,5RS,6RS)-2,2-ethylenedithio-4-hydroxybicyclo[3.1.0]hexane-6-carboxylate.

The $^1$H-NMR spectral data of the obtained compounds are shown below.

$^1$H-NMR (CDCl$_3$) δ (ppm); 1.26 (3H×5/8, t, J=7.1 Hz), 1.28 (3H×3/8, t, J=7.1 Hz), 1.53 (1H×5/8, t, J=3.1 Hz), 1.70–2.54 (5H+1H×3/8, m), 3.28–3.50 (4H, m), 4.13 (2H×3/8, q, J=7.1 Hz), 4.14 (2H×5/8, q, J=7.1 Hz), 4.36 (1H×5/8, dd, J=7.5, 4.8 Hz), 4.64 (1H×3/8, m).

Example 3

Synthesis of Ethyl (1RS,5RS,6RS)-4,4-Ethylenedithio-2-oxobicyclo[3.1.0]hexane-6-carboxylate To a dimethylsulfoxide (520 mL) solution of 13.1 g of a mixture of ethyl (1RS,4RS,5RS,6RS)-2,2-ethylenedithio-4-hydroxybicyclo[3.1.0]hexane-6-carboxylate and ethyl (1RS,4SR,5RS,6RS)-2,2-ethylenedithio-4-hydroxybicyclo[3.1.0]hexane-6-carboxylate, 40.5 g of dicyclohexylcarbodiimide, 5.0 mL of pyridine, and 2.8 mL of trifluoroacetic acid were successively added at 15° C. The reaction mixture was stirred for one day at room temperature, and subsequently, the precipitated solids were separated by filtration and were washed with ethyl acetate. The filtrate and the ethyl acetate used for washing were combined and poured into water, followed by extraction with chloroform. The organic layer was washed with water three times and was subsequently dried over anhydrous sodium sulfate. After the desiccant was filtered off, the filtrate was concentrated under reduced pressure. The residue was purified by silica gel column chromatography (Wako gel C$_{200}$ (produced by Wako pure Chemical Industries Ltd.), eluent: hexane-ethyl acetate=5:1) to yield 10.5 g of ethyl (1RS,5RS,6RS)-4,4-ethylenedithio-2-oxobicyclo[3.1.0]hexane-6-carboxylate.

The $^1$H-NMR and MS spectral data of the obtained compound are shown below.

$^1$H-NMR (CDCl$_3$) δ (ppm); 1.29 (3H, t, J=7.1 Hz), 2.25 (1H, dd, J=3.3, 2.8 Hz), 2.53 (1H, dd, J=5.5, 2.8 Hz), 2.75 (2H, s), 3.01 (1H, dd, J=5.5, 3.3 Hz), 3.37–3.53 (4H, m), 4.18 (2H, dq, J=2.2, 7.1 Hz). MS (FAB) (Pos.) m/e; 259 (M$^+$+1).

Ethyl (1RS,5RS,6RS)-4,4-ethylenedithio-2-oxobicyclo[3.1.0]hexane-6-carboxylate may be optically resolved into ethyl (1R*, 5R*,6R*)-4,4-ethylenedithio-2-oxobicyclo[3.1.0]hexane-6-carboxylate (t$_R$: 7.65 min.) and ethyl (1R*, 5R*,6R*)-4,4-ethylenedithio-2-oxobicyclo[3.1.0]hexane-6-carboxylate (t$_R$: 9.17 min.), respectively, by use of the HPLC (CHIRALPAK AD 0.46*25 cm (produced by Daicel Chemical Industries, Ltd.), Eluent: n-hexane/2-propanol=3:1, Flowrate: 1.0 mL/min., Temp.: rt., Detect: UV 210 nm).

Example 4

Synthesis of Ethyl (1RS,2SR,5RS,6RS)-2-Spiro-5'-hydantoin-4,4-ethylenedithiobicyclo[3.1.0]hexane-6-carboxylate A mixture of 73.2 g of ethyl (1RS,5RS,6RS)-4,4-ethylenedithio-2-oxobicyclo[3.1.0]hexane-6-carboxylate, 68.1 g of ammonium carbonate, and 20.8 g of potassium cyanide was stirred in a mixed solvent of 460 mL of ethanol and 307 mL of water for 3 days at 35° C. The reaction mixture was stirred for 2 hours at 0° C., and subsequently, the precipitated solids were collected by filtration. The obtained solids were stirred in 1.1 L of a mixed solvent of chloroform-methanol (9:1) for 1.5 hours at 65° C. and were subsequently cooled down to room temperature. The precipitated crystals were collected by filtration. The crystals were subjected to the same procedure as described above in 100 mL of a mixed solvent of chloroform-methanol (9:1) to yield 35.2 g of ethyl (1RS,2SR,5RS,6RS)-2-spiro-5'-hydantoin-4,4-ethylenedithiobicyclo[3.1.0]hexane-6-carboxylate.

The $^1$H-NMR and MS spectral data of the obtained compound are shown below.

$^1$H-NMR (DMSO-d$_6$) δ (ppm); 1.20 (3H, t, J=7.0 Hz), 2.00 (1H, t, J=3.1 Hz), 2.21 (1H, d, J=16 Hz), 2.25–2.29 (1H, m, J=3.1 Hz), 2.46 (1H, dd, J=6.2 Hz, 3.1 Hz), 2.60 (1H, d, J=16Hz), 3.20–3.42 (4H, m), 4.07 (2H, q, J=7.0 Hz), 7.91 (1H, s), 10.70 (1H, s). MS (Ion Spray) (Nega) m/e; 327 (M$^+$−1).

Example 5

Synthesis of (+)-(1S,2S,5R,6R)-2-Amino-4-oxobicyclo[3.1.0]hexane-2,6-dicarboxylic Acid (1) A mixture of 2.10 g of ethyl (1RS,2SR,5RS,6RS)-2-spiro-5'-hydantoin-4,4-ethylenedithiobicyclo[3.1.0]hexane-6-carboxylate and 13 mL of a 2N aqueous solution of sodium hydroxide was stirred for one hour at room temperature. Subsequently, concentrated hydrochloric acid was added to the mixture to adjust the pH thereof to pH 1.0. The generated crystals were separated by filtration and were washed with 70 mL of water, followed by drying to yield 1.87 g of (1RS,2SR,5RS,6RS)-2-spiro-5'-hydantoin-4,4-ethylenedithiobicyclo[3.1.0]hexane-6-carboxylic acid.

(2) In 50 mL of N,N-dimethylformamide, 1.87 g of (1RS,2SR,5RS,6RS)-2-spiro-5'-hydantoin-4,4-ethylenedithiobicyclo[3.1.0]hexane-6-carboxylic acid and 0.91 g of (R)-(+)-1-phenylethylamine were dissolved, and subsequently, 1.05 g of 1-hydroxybenzotriazole monohydrate and 1.43 g of 1-ethyl-3-(3-dimethylaminopropyl) carbodiimide hydrochloride were added thereto with ice-cooling. The reaction mixture was stirred for 14 hours at room temperature. The reaction mixture was added to 1N hydrochloric acid and was subsequently extracted with ethyl acetate. The organic layer was dried over anhydrous sodium sulfate. After the desiccant was filtered off, the filtrate was concentrated under reduced pressure. The residue was subjected to silica gel column chromatography (silica gel: MSG40–60A (produced by Dokai Chemical Industries Ltd.), eluent: chloroform-methanol=40:1 to 25:1) to separate into 1.17 g of (1S,2R,5S,6S)-2-spiro-5'-hydantoin-4,4-ethylenedithio-N-((R)-1-phenylethyl)-bicyclo[3.1.0]hexane-6-carboxyamide (Rf value 0.54 (TLC: Silica gel 60 $F_{254}$ (produced by Merck & Co., Inc.), eluent: chloroform-methanol=9:1)) and 1.10 g of (1R,2S,5R,6R)-2-spiro-5'-hydantoin-4,4-ethylenedithio-N-((R)-1-phenylethyl)-bicyclo[3.1.0]hexane-6-carboxyamide (Rf value 0.51 (TLC: Silica gel 60 $F_{254}$ (produced by Merck & Co., Inc.), eluent: chloroform-methanol=9:1)).

(3) In 20 mL of a 60% (w/v %) aqueous solution of sulfuric acid, 1.10 g of (1R,2S,5R,6R)-2-spiro-5'-hydantoin-4,4-ethylenedithio-N-((R)-1-phenylethyl)-bicyclo[3.1.0]hexane-6-carboxyamide obtained in (2) described above was suspended. The suspension was stirred for 4 days at 145° C. The reaction mixture was allowed to cool down to room temperature, and subsequently, the pH thereof was adjusted to pH 7 with a 5N aqueous solution of sodium hydroxide. Subsequently, the reaction mixture was subjected to an ion exchange chromatography (AG1-X8 anion exchange resin (Bio-Rad), OH⁻ form, eluent: water to 50% tetrahydrofuran—water to water to a 30% aqueous solution of acetic acid) to yield 0.37 g of crystals. To the crystals, 10 mL of acetone was added, and the mixture was stirred for 2 hours at room temperature. Subsequently, the crystals were separated by filtration and then washed with 5 mL of acetone, 5 mL of tetrahydrofuran, and 5 mL of acetone, followed by drying to yield 0.30 g of (+)-(1S,2S,5R,6R)-2-amino-4-oxobicyclo[3.1.0]hexane-2,6-dicarboxylic acid.

The $^1$H-NMR, MS spectral, and specific optical rotation value data of the obtained compound are shown below.

$^1$H-NMR (pyridine-$d_5$/$D_2O$=1/1) δ (ppm); 2.86 (1H, dd, J=3.5 Hz, 2.7 Hz), 2.93 (1H, d, J=18 Hz), 3.00 (1H, dd, J=5.7 Hz, 2.7 Hz), 3.05 (1H, d, J=18 Hz), 3.30 (1H, dd, J=5.7 Hz, 3.5 Hz). MS (FAB) (Nega.) m/e; 198 (M⁺−1). $[α]_D^{32}$=+43.06 (c=0.20, $H_2O$).

Industrial Applicability

The compounds according to the present invention, bicyclo[3.1.0]hexane-6-carboxylic acid derivatives are useful as intermediates for synthesis of 4-substituted-2-aminobicyclo[3.1.0]hexane-2,6-dicarboxylic acids acting on group 2 metabotropic glutamate receptors, which have treatment effects and prevention effects on psychiatric disorders such as, for example, schizophrenia, anxiety and its associated diseases, depression, bipolar disorder, and epilepsy; and neurological diseases such as drug dependence, cognitive disorders, Alzheimer's disease, Huntington is chorea, Parkinson's disease, dyskinesia associated with muscular rigidity, cerebral ischemia, cerebral failure, myelopathy, and head trauma.

In addition, in the case where 2-oxobicyclo[3.1.0]hexane-6-carboxylic acid derivatives are employed as starting materials, 2-amino-4-oxobicyclo[3.1.0]hexane-2,6-dicarboxylic acids can be produced efficiently, and in particular, optically active substances can be synthesized in good yield.

What is claimed is:

1. A 2-oxobicyclo[3.1.0]hexane-6-carboxylic acid compound represented by formula (1)

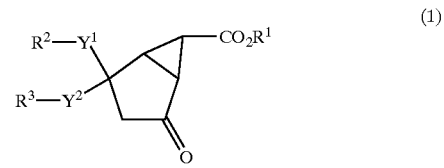

(1)

wherein, $R^1$ represents a hydrogen atom, a $C_1$–$C_6$ alkyl group, a $C_3$–$C_6$ cycloalkyl group, a $C_3$–$C_6$ cycloalkyl $C_1$–$C_6$ alkyl group, an aryl group, an aryl $C_1$–$C_6$ alkyl group, a $C_1$–$C_6$ alkoxy $C_1$–$C_6$ alkyl group, a $C_1$–$C_6$ hydroxyalkyl group, a $C_1$–$C_6$ alkylthio $C_1$–$C_6$ alkyl group, a $C_1$–$C_6$ mercaptoalkyl group, a tetrahydrofuranyl group, or a tetrahydropyranyl group; $R^2$ and $R^3$ are identical or different, and each represents a $C_1$–$C_6$ alkyl group, a $C_3$–$C_6$ cycloalkyl group, a $C_3$–$C_6$ cycloalkyl $C_1$–$C_6$ alkyl group, an aryl group, or an aryl $C_1$–$C_6$ alkyl group, or $R^2$ and $R^3$ together represent —($CH_2$)$_n$— (wherein n represents 2 or 3); and $Y^1$ and $Y^2$ are identical or different, and each represents a sulfur atom, an oxygen atom, or a nitrogen atom.

2. A process for producing the carboxylic acid compound according to claim 1, comprising the steps of:

reacting a cyclopentenone compound represented by formula (2)

(2)

wherein, $R^4$ represents a hydrogen atom or a protecting group of the hydroxyl group with a sulfonium ylide represented by $Me_2S$=$CHCO_2R^5$ wherein, $R^5$ represents a $C_1$–$C_6$ alkyl group, a $C_3$–$C_6$ cycloalkyl group, a $C_3$–$C_6$ cycloalkyl $C_1$–$C_6$ alkyl group, an aryl group, an aryl $C_1$–$C_6$ alkyl group, a $C_1$–$C_6$ alkoxy $C_1$–$C_6$ alkyl group, a $C_1$–$C_6$ hydroxyalkyl group, a $C_1$–$C_6$ alkylthio $C_1$–$C_6$ alkyl group, a $C_1$–$C_6$ mercaptoalkyl group, a tetrahydrofuranyl group, or a tetrahydropyranyl group] or, with a sulfonium salt represented by $Me_2S^+$ $CH_2CO_2R^5$. $X^-$ wherein, $R^5$ is the same as described above; and X represents a chlorine atom, a bromine atom, or an iodine atom to yield a bicyclo compound represented by formula (3)

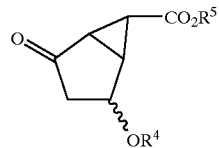
(3)

wherein, $R^4$ and $R^5$ are the same as described above;

protecting the carbonyl group of said bicyclo compound to yield a compound represented by formula (4)

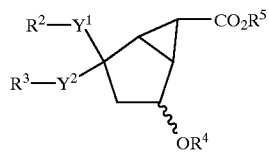
(4)

wherein, $R^2$ and $R^3$ are identical or different, and each represents a $C_1$–$C_6$ alkyl group, $C_3$–$C_6$ cycloalkyl group, a $C_3$–$C_6$ cycloalkyl $C_1$–$C_6$ alkyl group, an aryl group, or an aryl $C_1$–$C_6$ alkyl group, or, $R^2$ and $R^3$ together represent —$(CH_2)_n$— (wherein n represents 2 or 3); $Y^1$ and $Y^2$ are identical or different, and each represents a sulfur atom, an oxygen atom, or a nitrogen atom; and $R^4$ and $R^5$ are the same as described above; and oxidizing said compound wherein $R^4$ represents a hydrogen atom, with the proviso that in the case of $R^4$ of said compound representing a group other than a hydrogen atom, the $R^4$ is converted into a hydrogen atom beforehand.

* * * * *